United States Patent [19]

Takahashi et al.

[11] Patent Number: 5,368,727
[45] Date of Patent: Nov. 29, 1994

[54] LIQUID CHROMATOGRAPH MASS SPECTROMETER

[75] Inventors: Toshiaki Takahashi; Kenichi Shizukuishi; Youko Katho; Naoto Senda, all of Katsuta; Tomomi Bando, Mito, all of Japan

[73] Assignees: Hitachi, Ltd., Tokyo; Hitachi Instruments Engineering Co., Ltd., Ibaraki, both of Japan

[21] Appl. No.: 955,148

[22] Filed: Sep. 29, 1992

[30] Foreign Application Priority Data

Oct. 3, 1991 [JP] Japan .................. 3-256409

[51] Int. Cl.$^5$ ............... B01D 15/08; B01D 59/44; G06F 15/46
[52] U.S. Cl. ................... 210/198.2; 210/85; 250/288; 364/497; 364/500
[58] Field of Search .......... 210/85, 138, 143, 198.2; 250/288, 288 A; 364/500, 502, 557, 497, 498; 73/61.52

[56] References Cited

U.S. PATENT DOCUMENTS

| | | | |
|---|---|---|---|
| 4,854,498 | 8/1989 | Stayton | 364/502 |
| 4,888,482 | 12/1989 | Kato | 250/288 |
| 4,980,057 | 12/1990 | Dorn et al. | 210/198.2 |
| 4,996,424 | 2/1991 | Mimura et al. | 250/288 A |

FOREIGN PATENT DOCUMENTS 59-210358 11/1984 Japan .
63-241849 10/1988 Japan .

Primary Examiner—Sun Uk Kim
Attorney, Agent, or Firm—Antonelli, Terry, Stout & Kraus

[57] ABSTRACT

A liquid chromatograph mass spectrometer includes a liquid chromatograph unit for performing liquid chromatography, an atomizer having a controllable temperature for heating and atomizing a liquid flowing out of the liquid chromatograph unit during liquid chromatography to produce an atomized liquid, an ionizing device for ionizing the atomized liquid to produce an ionizing sample, a mass spectrometer for analyzing the ionized sample, a storage device for successively storing liquid chromatography conditions and respective atomizer temperatures used for the liquid chromatography conditions for past measurements performed with the liquid chromatograph mass spectrometer, an input device for inputting a current liquid chromatography condition for a current measurement, a retrieving device for retrieving from the storage device a liquid chromatography condition nearest to the current liquid chromatography condition among the liquid chromatography conditions stored in the storage device, and the atomizer temperature used for the retrieved liquid chromatography condition, and an atomizer temperature setting device for setting the atomizer temperature to an optimum temperature for the current liquid chromatography condition based on the retrieved atomizer temperature.

5 Claims, 3 Drawing Sheets

LIQUID CHROMATOGRAPH MASS SPECTROMETER

BACKGROUND OF THE INVENTION

1. Field of the Invention

The present invention relates to a liquid chromatograph-mass spectrometer using, for example, the atmospheric pressure ionization method.

2. Description of Related Art

A specimen component which flows out from a liquid chromatograph unit arrives at an atomizer together with a traveling phase solvent via a Teflon pipe. The atomizer is heated to a temperature of 180°~330° C. whereby the specimen component and the traveling phase solvent are heated and atomized. The atomized specimen component and traveling phase solvent subsequently arrive at a desolvent chamber wherein most of the traveling phase solvent is vaporized and removed and the remaining components are then introduced into an atmospheric pressure ionization chamber. In the atmospheric pressure ionization chamber, a needle electrode for causing corona discharge is provided, and via the corona discharge the solvent molecules are ionized. From the solvent ions thus produced, electric charges are transferred to the specimen molecules whereby the specimen molecules are ionized. The ionized specimen molecules thus produced are introduced into the main body of a mass spectrometer via an intermediate pressure region, and the result of mass spectrometry is outputted from a data processing device or central processing unit (CPU) in the form of a mass spectrum.

The heating temperature of the atomizer is determined depending upon the boiling temperature and the heat of vaporization of a traveling phase solvent to be used. Thereby, an optimum temperature which causes a stable atomization varies depending upon the kind of the traveling phase solvent and the mixture ratio thereof when the traveling phase solvent is composed of two or more components. Further, in the case of a gradient measurement wherein the mixture ratio of the traveling phase solvent varies depending upon time, the optimum heating temperature of the atomizer also varies depending upon time.

In the atmospheric pressure ionization method, the temperature of the atomizer greatly affects the detection sensitivity of a specimen so that a correct temperature setting is very important for obtaining a desirable spectrum of the specimen.

In the conventional liquid chromatograph mass spectrometer, the temperature of the atomizer is manually set and controlled by a person performing the measurement via an atomizer temperature controller.

Examples of the liquid chromatograph mass spectrometer using the atmospheric pressure ionization method are disclosed in JP-A-59-210358 (1984) and JP-A-63-241849 (1988).

In the conventional liquid chromatograph mass spectrometer of this kind, the temperature of the atomizer is manually set by a person performing the measurement solely depending upon his or her experience. Namely, the conventional atomizer temperature controller is constituted independently from the CPU serving as the data processing device and a manual temperature setting is performed via the atomizer temperature controller. For this reason, there is a problem that the temperature setting is difficult for beginners. Further when a gradient analysis with the liquid chromatograph mass spectrometer is required to be performed, it is necessary to vary the atomizer temperature depending upon the mixture ratio of a traveling phase solvent, but there is no provision for changing the atomizer temperature rapidly and stably.

SUMMARY OF THE INVENTION

The present invention has been achieved in view of the above problems. An object of the present invention is to provide a liquid chromatograph mass spectrometer which sets an optimum atomizer temperature in response to a liquid chromatography condition (hereinbelow abbreviated as LC condition) inputted by a person performing the measurement.

For achieving the above object, the liquid chromatograph mass spectrometer according to the present invention which is designed to heat and atomize the liquid flowing out from the liquid chromatograph unit and thereafter to ionize the same to analyze the same in the mass spectrometer comprises a storage means which successively stores at every measurement the LC condition and the temperature used at a heating atomizer at that instant; means for retrieving the nearest LC condition to the LC condition inputted by an operator for the present measurement among the past measurement examples stored in the storage means; and a temperature setting means which sets an optimum atomizer temperature applied for the present measurement based upon the atomizer temperature corresponding to the retrieved LC condition.

The temperature setting means is realized, for example, by incorporating such a function into the CPU in a computer which performs data processing on the result of the mass spectrometry, and the means for storing the past measurement examples is realized, for example, by a RAM.

When a person performing the measurement inputs an LC condition, the past measurement examples in the data relating to LC conditions and atomizer temperatures which were stored beforehand in the storage means are called up and collated with the inputted LC condition, and the nearest LC condition thereto is retrieved. The temperature setting means sets an optimum atomizer temperature for the present measurement based upon the atomizer temperature corresponding to the retrieved LC condition. The atomizer temperature setting is performed in the following manner. When there exists a near or identical LC condition to the present LC condition among the past measurement examples, the atomizer temperature corresponding to the retrieved near or identical LC condition is used as it is. However, when no near LC conditions to the present LC condition exist among the past measurement examples, the person performing the measurement has to set the atomizer temperature based upon his or her experience, and the set atomizer temperature is stored in the storage means in order to accumulate atomizer temperature data for subsequent measurements. As an alternative thereto, the CPU may be provided with a processing function which estimates an atomizer temperature suitable for the present LC condition with reference to the stored past measurement examples and determines the estimated atomizer temperature as the set temperature, even when there are no near LC conditions to the present LC condition among the past measurement examples.

Then, a command signal is sent out from the temperature setting means to a power source for heating the atomizer so that the atomizer assumes the set atomizer temperature and the power source for heating the atomizer heats the atomizer up to the set temperature according to the command signal.

When the LC condition relates to a gradient analysis, data relating to the temperature used therefor in an atomizer temperature lowering characteristic as well as the LC condition at that moment are stored together and are used as data for determining the subsequent atomizer temperature setting as explained above.

Further, when a gradient analysis with a liquid chromatograph mass spectrometer is performed, a person performing the measurement can prepare a temperature lowering program and input the same as an LC condition, and the temperature setting means can be designed to send out a command signal to a power source for a temperature lowering means, for example a fan for cooling the atomizer to lower the atomizer temperature based upon the program and in accordance with the lapse of time.

DESCRIPTION OF THE PREFERRED EMBODIMENT

Figure 1:
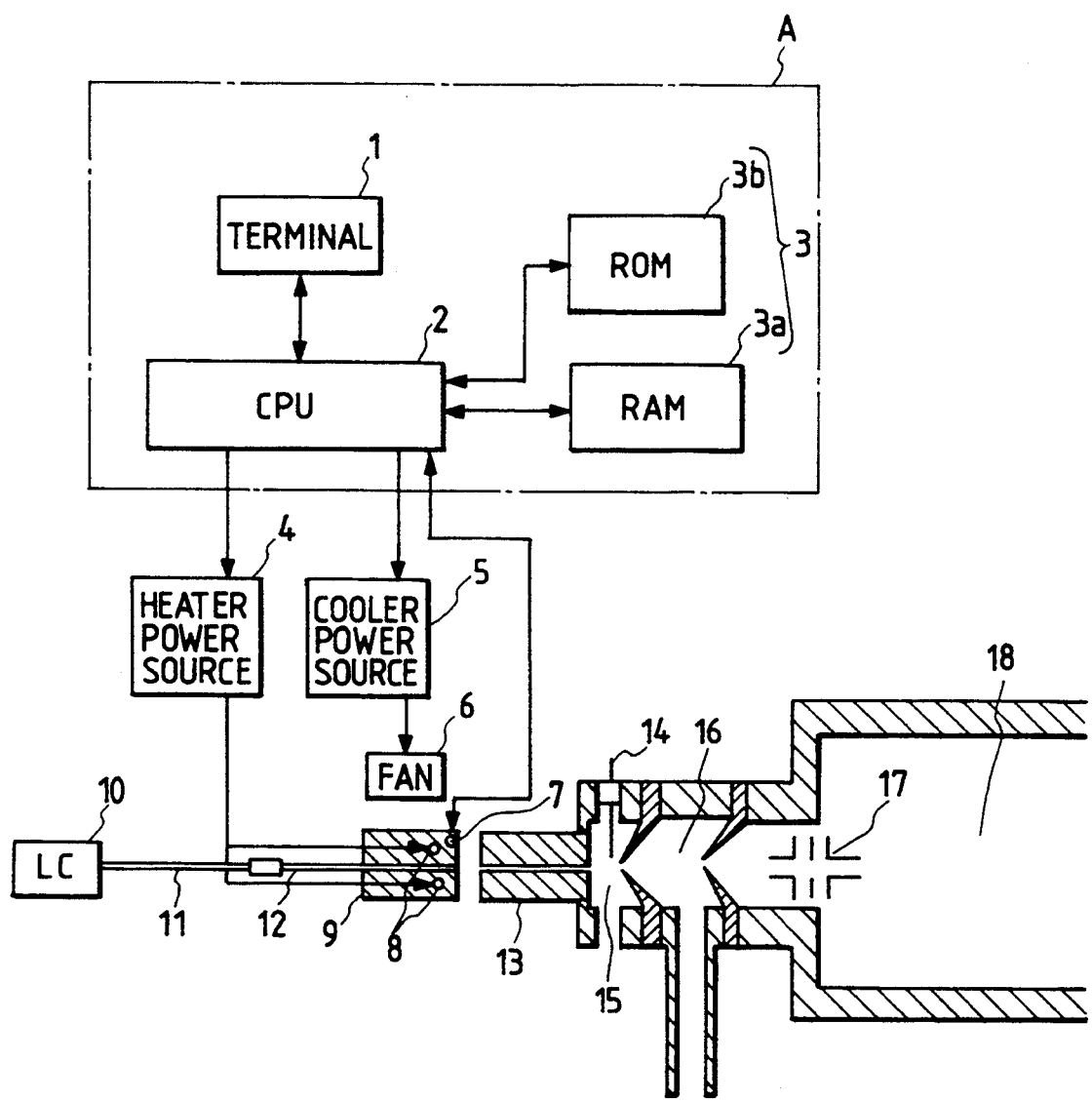
FIG. 1 is a constitutional diagram of one embodiment of a liquid chromatograph mass spectrometer according to the present invention.

In FIG. 1, a computer A comprises an I/O terminal unit 1, a central processing unit (CPU) 2, and a storage unit 3 including a RAM 3a and a ROM 3b. A person performing the measurement inputs an LC condition to the CPU 2 via the I/O terminal unit 1. On the other hand, the RAM 3a is provided with a function of successively storing LC conditions for mass spectrometry and the atomizer temperatures used therefor. Herein, the LC conditions which are to be stored include the LC conditions relating to gradient analyses and the atomizer temperature lowering characteristics therefor.

Besides a data processing function which processes the result of mass spectrometry, i.e. the measured data from a mass spectrometer main body 18, and outputs a mass spectrum based upon the input, the CPU 2 is provided with a function in which when an LC condition is inputted from the I/O terminal unit 1, the newly inputted LC condition is collated with many measured examples of the past LC conditions stored in the RAM 3a and the nearest past LC condition, either a coincident one or a similar one, to the newly inputted LC condition is retrieved, and is provided with another function which sets an optimum temperature for an atomizer 9 based upon the atomizer temperature used under the retrieved LC condition.

Further, the CPU 2 sends out a command signal to an atomizer heating power source 4 and if necessary to an atomizer cooling power source 5 so that the atomizer 9 assumes the set atomizer temperature. Herein, the atomizer heating power source 4 supplies electric power to a heater 8 built into the atomizer 9 and the atomizer cooling power source 5 supplies electric power to a blower or cooling fan 6 for cooling the atomizer 9 disposed near the atomizer 9. The cooling fan 6 is used for gradient mass spectrometry in which mass spectrometry is performed by making use of an atomizer temperature gradient. Namely, the CPU 2 controls the current conduction through the heater 8 according to the set temperature when mere atomization is required, and when gradient mass spectrometry is required to be performed, the CPU 2 controls the current conduction through the heater 8 and the fan 6 according to the set temperature lowering program, such that through these current conduction controls, the temperature of the atomizer 9 is adjusted at the optimum temperature. A temperature sensor 7 is disposed at the atomizer for monitoring the temperature thereof and the detected signal thereof is inputted to the CPU 2.

Figure 2A:
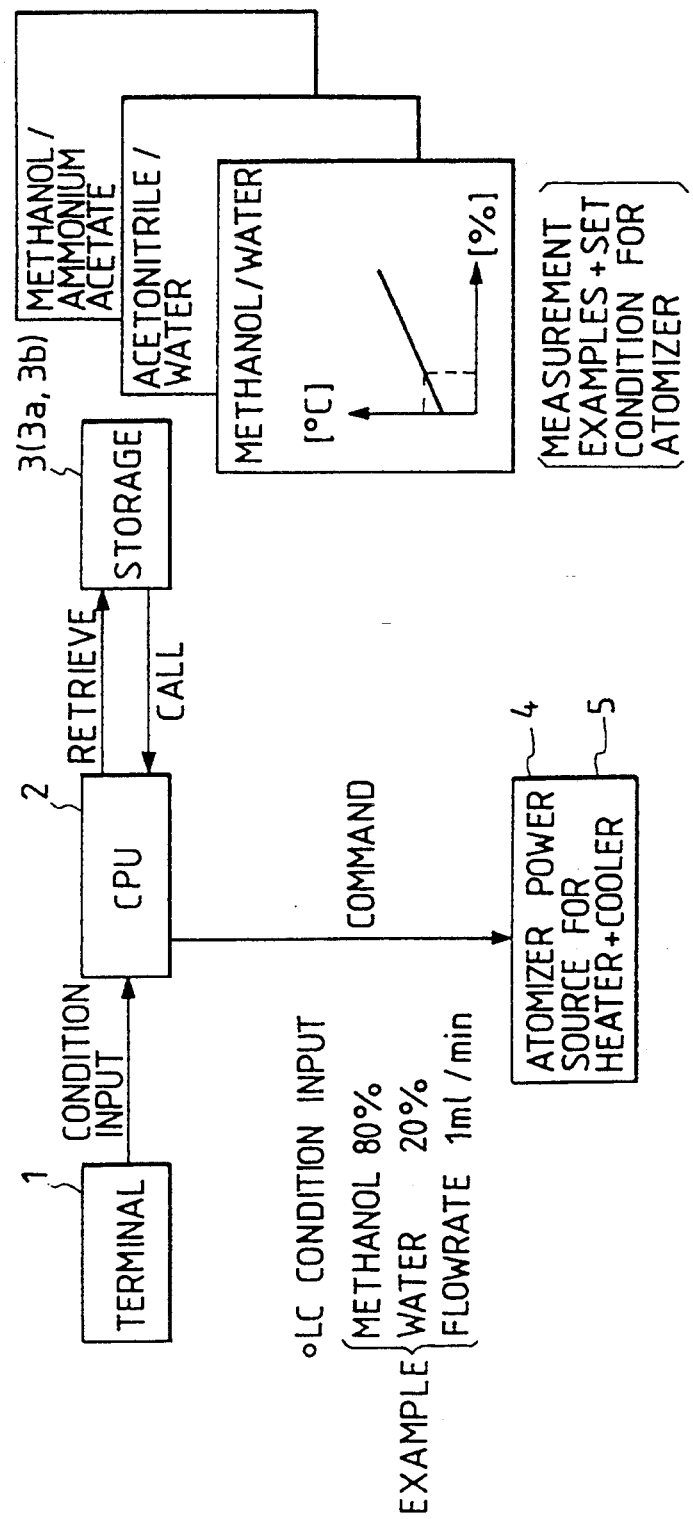
FIGS. 2(a)-2(b) are explanatory views illustrating manners of atomizer temperature setting in the embodiment shown in FIG. 1.

FIG. 2(a) shows a relationship between the I/O terminal 1, CPU 2, storage unit 3 including the RAM 3a and ROM 3b and the atomizer heating and cooling power sources 4 and 5 for setting the atomizer temperature during measurement under a non-gradient LC condition.

Figure 2B:
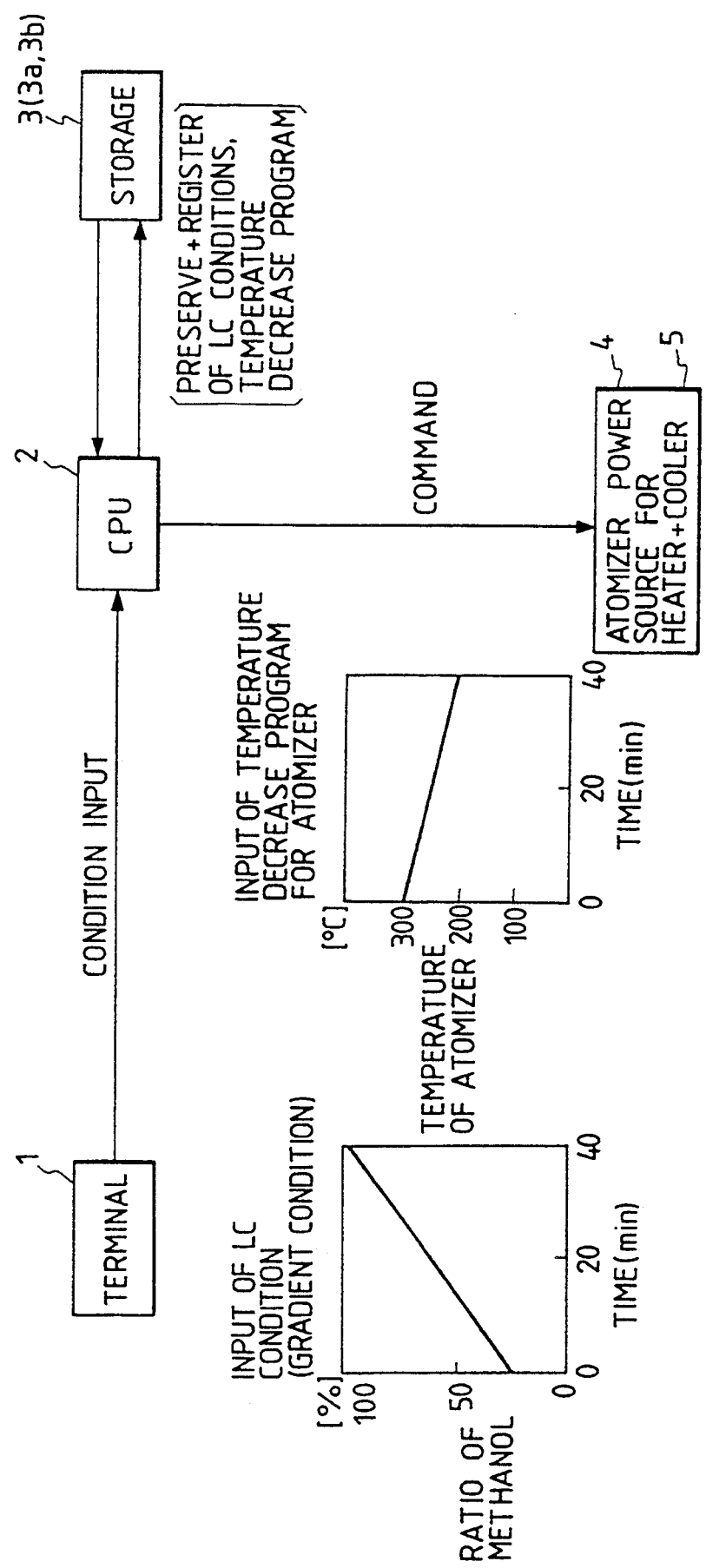

FIG. 2(b) shows a relationship between the same constituents as above for setting the atomizer temperature during measurement under a gradient LC condition.

When performing gradient mass spectrometry with the liquid chromatograph mass spectrometer of the present embodiment, as illustrated in Fig. 2(b), a person performing the measurement inputs an atomizer temperature lowering program prepared beforehand into the CPU 2 via the I/O terminal unit 1. The CPU 2 transfers the atomizer temperature lowering program to the RAM 3a to store the same therein and outputs a command signal to the cooling fan power source 5 for lowering the atomizer temperature in accordance with the lapse of time based upon the inputted atomizer temperature lowering program. The atomizer temperature lowering program stored in the RAM 3a can be called at any time for use in subsequent measurements.

The traveling phase solvent and the specimen component which flow out from a liquid chromatograph unit 10 pass through a Teflon pipe 11 and a stainless steel micro pipe 12 and thereafter arrives at the atomizer 9 which is controlled to have an optimum temperature as explained previously. In the atomizer 9, the traveling phase solvent and the specimen component are heated and atomized under an optimum and stable condition. The atomized traveling phase solvent and the specimen component advance into a desolvent chamber 13 in which the substantial part of the traveling phase solvent is vaporized and discharged from the device. The remaining traveling phase solvent and the specimen component further advance into an atmospheric pressure ionization chamber 15 in which ionization of the remaining traveling phase solvent is induced via corona discharge generated at the top end of a needle electrode 14 to which a high electrical voltage is applied. Subsequently, the electric charges of the traveling phase solvent move to the specimen component to cause ionization of the specimen component. The generated ions of the specimen component pass through an intermediate pressure chamber 16 and are focused by a lens electrode 17 and thereafter sent to the mass spectrometer main body 18.

According to the present embodiment, the person performing the measurement is only required to input an LC condition, and in accordance with the inputted LC condition, the CPU 2 sets an optimum atomizer temperature. Therefore, a beginner who has little experience with regard to measurement with a liquid chromatograph mass spectrometer can easily perform the measurement and obtain a desirable measurement result. Further, when a gradient analysis is required, with the provision of the atomizer cooling fan 6 which is controlled by the CPU 2, an analysis in which the atomizer temperature is lowered depending upon the gradient change can be performed. Still further, the atomizer temperature is set at an optimum atomizer temperature based upon the retrieved data among the past measurement examples as well as the atomizer temperature lowering program prepared or stored, and therefore the traveling phase solvent under any LC condition is always heated and atomized at an optimum condition. Accordingly, the specimen component is ionized stably and at a high efficiency, and a desirable mass spectrum is obtained.

We claim:

1. A liquid chromatograph mass spectrometer comprising:
 a liquid chromatograph unit for performing liquid chromatography;
 an atomizer having a controllable temperature for heating and atomizing a liquid flowing out of the liquid chromatograph unit during liquid chromatography to produce an atomized liquid;
 ionizing means for ionizing the atomized liquid to produce an ionized sample;
 a mass spectrometer for analyzing the ionized sample;
 storage means for successively storing liquid chromatography conditions and respective atomizer temperatures used for the liquid chromatography conditions for past measurements performed with the liquid chromatograph mass spectrometer;
 input means for inputting a current liquid chromatography condition for a current measurement;
 retrieving means for retrieving from the storage means a liquid chromatography condition nearest to the current liquid chromatography condition among the liquid chromatography conditions stored in the storage means, and the atomizer temperature used for the retrieved liquid chromatography condition; and
 atomizer temperature setting means for setting the atomizer temperature to an optimum temperature for the current liquid chromatography condition based on the retrieved atomizer temperature.

2. A liquid chromatograph mass spectrometer according to claim 1, wherein the storage means stores a gradient liquid chromatography condition and an atomizer temperature lowering program used to lower the atomizer temperature over time for the gradient liquid chromatography condition for a past measurement;
 wherein the retrieving means is capable of retrieving the atomizer temperature lowering program stored in the storing means;
 wherein the input means inputs a current gradient liquid chromatography condition for a current measurement and is capable of inputting an atomizer temperature lowering program for the current gradient liquid chromatography condition; and
 wherein the atomizer temperature setting means lowers the atomizer temperature over time for the current gradient liquid chromatography condition in accordance with a selected one of (1) the atomizer temperature lowering program stored in the storage means and retrieved by the retrieving means, and (2) the atomizer temperature lowering program inputted by the input means.

3. A liquid chromatograph mass spectrometer according to claim 1, wherein the atomizer temperature setting means includes a blower fan for cooling the atomizer to lower atomizer temperature over time in accordance with the selected atomizer temperature lowering program.

4. A liquid chromatograph mass spectrometer comprising:
 a liquid chromatograph unit for performing liquid chromatography;
 an atomizer having a controllable temperature for heating and atomizing a liquid flowing out of the liquid chromatograph unit during liquid chromatography to produce an atomized liquid;
 ionizing means for ionizing the atomized liquid to produce an ionized sample;
 a mass spectrometer for analyzing the ionized sample;
 an atomizer temperature controller for controlling the atomizer temperature in response to a control signal; and
 a computer, the computer including
 a central processing unit,
 a storage unit, and
 an I/O terminal unit for inputting a current liquid chromatography condition for a current measurement,
 wherein the central processing unit
 successively stores in the storage unit liquid chromatography conditions and respective atomizer temperatures used for the liquid chromatography conditions for past measurements performed with the liquid chromatograph mass spectrometer,
 retrieves from the storage unit a liquid chromatography condition nearest to the current liquid chromatography condition among the liquid chromatography conditions stored in the storage unit, and the atomizer temperature used for the retrieved liquid chromatography condition, and
 outputs to the atomizer temperature controller a control signal for causing the atomizer temperature controller to set the atomizer temperature to an optimum temperature for the current liquid chromatography condition based on the retrieved atomizer temperature.

5. A liquid chromatograph mass spectrometer comprising:
 a liquid chromatograph unit for performing liquid chromatography;
 an atomizer having a controllable temperature for heating and atomizing a liquid flowing out of the liquid chromatograph unit during liquid chromatography to produce an atomized liquid;
 ionizing means for ionizing the atomized liquid to produce an ionized sample;
 a mass spectrometer for analyzing the ionized sample;
 an atomizer temperature controller for controlling the atomizer temperature in response to a control signal;
 a storage unit for successively storing liquid chromatography conditions and respective atomizer temperatures used for the liquid chromatography conditions for past measurements performed with the liquid chromatograph mass spectrometer;
 an I/O terminal unit for inputting a current liquid chromatography condition for a current measurement; and
 a central processing unit for retrieving from the storage unit a liquid chromatography condition nearest to the current liquid chromatography condition among the liquid chromatography conditions stored in the storage unit, and the atomizer temperature used for the retrieved liquid chromatography condition, and outputting to the atomizer temperature controller a control signal for causing the atomizer temperature controller to set the atomizer temperature to an optimum temperature for the current liquid chromatography condition based on the retrieved atomizer temperature.

* * * * *